United States Patent [19]

Vletter

[11] Patent Number: Plant 7,151

[45] Date of Patent: Feb. 13, 1990

[54] *ERYNGIUM PLANUM* PLANT NAMED BLUE RIBBON

[75] Inventor: Floris Vletter, Rijnsburg, Netherlands

[73] Assignee: de Vennootschap Onder Firma Gebr, Vletter & J. A. Den Haan, Netherlands

[21] Appl. No.: 260,695

[22] Filed: Oct. 21, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A distinct cultivar of *Eryngium planum* named Blue Ribbon, characterized by its flower head which has very unique umbel formations, large and long peduncles with secondary and tertiary branches, medium violet mature flower color, and its rosette base.

3 Drawing Sheets

1

The present invention comprises a new and distinct cultivar of *Eryngium planum,* commonly called sea holly, and known by the cultivar name Blue Ribbon.

Blue Ribbon was discovered by the inventor Floris Vletter in July 1983 in a controlled environment in Rijnsburg, the Netherlands a a mutation of Fluela, a cultivar of the inventor disclosed in a pending application. Blue Ribbon was discovered growing among plants of the parent cultivar and was particularly noted by the absence of the relatively large ellipsoidal shaped single flower heads of the parent cultivar. Rather, the new cultivar was particularly characterized by irregularly shaped compound umbels containing clusters of small flowers. The entire inflorescence therefore appears much fuller. The mature flower color of Blue Ribbon is also a shade lighter purple than the parent cultivar.

The first act of asexual reproduction of Blue Ribbon was accomplished when root cuttings were taken from the selected discovery on Aug. 3, 1983 in a controlled environment in Rijnsburg, the Netherlands by a technician working under formulations established and supervised by the inventor. Horticultural examination of selected units, initiated on Sept. 11, 1986 has demonstrated that the combination of characteristics as herein disclosed for Blue Ribbon are firmly fixed and are retained through successive generations of asexual reproduction.

Blue Ribbon has not been observed under all possible environmental conditions. The phenotype may vary considerably with variations in environment such as temperature, light intensity and day length. The following observations, measurements and comparisons describe plants grown in Wageningen, the Netherlands under outside conditions which approximate those generally used in commercial practice. Color references are made to The Royal Horticultural Society Colour Chart.

The accompanying photographic drawings show a typical specimen plant of the new cultivar, with colors being as true as possible for color illustrations of this type.

Photographic Drawing 1 is a perspective view of blossoming branches of this variety.

Photographic Drawing 2 depicts a mature leaf of the variety.

2

Photographic Drawing 3 is a perspective view of mature blossoms of the variety, in clustered configuration.

The following traits have been repeatedly observed and are determined to be basic characteristics of Blue Ribbon, which in combination distinguish this *Eryngium planum* as a new and distinct cultivar:

1. Instead of the ellipsoidal heads that characterize the parent and most other cultivars, Blue Ribbon has very unique umbel formations, each of which has numerous very small flowers. The overall appearance is strikingly dissimilar to the parent and other cultivars having flower heads which commonly characterize this species.
2. The peduncles are relatively large and long, and widely branching into secondary and tertiary branches. The peduncles have a blue tinge toward the top and the lateral branches are similar in color to the flowers.
3. The flowers mature from a light green through a greyish green to a very pleasant medium violet.
4. The involucral bracts at the base of the flowers are narrow and long.
5. Rosette leaves at base of plant.

Plant:

*Form.*—Relataively large in diameter, and comparatively rounded in appearance.

*Size.*—About 100 cm tall when fully mature.

*Growth habit.*—Rosette base is dense, and plant produces strong and large peduncles.

Leaves:

*Size.*—Rosette leaves about 15 cm long with petioles of about 15 cm.

*Color.*—Dark green and dull-glossy.

*Quantity.*—Approximately 25.

*Shape.*—Leaf almost elliptical, crenate with its margin slightly prickled; involucral leaves narrow and long.

Peduncle:

*Size.*—From 35 cm upwards, branching out wider and then with secondary and tertiary branches.

*Color.*—The main stem silvery-grey with a blue tinge increasing in intensity towards the top; lateral branches rather intense blue-purple, about RHS 86 B–C.

*Stem leaves.*—Stem leaves sessile, leaf blades at the base of the peduncle similar to those of the rosette leaves, ovate upwards along the peduncle and then palmately parted and sharply pricked.

Flowers:

*Size.*—Individual flowers are small, about 0.4 centimeters in height and about 0.5 centimeters in width.

*Form.*—Flowers are clustered together to form irregular compound umbels; total flower head relatively small but substantially larger than single flower head of parent and other cultivars;

bracts and involucral leaves narrow and long, approximately 86 B–C with greyish tinge.

*Color.*—Mature: About RHS 86 A–B. Immature: Upper and lower surfaces are both light green.

Propagation: The new cultivar is reproduced through successive breeding generations by root cuttings.

I claim:

1. A new and distinct cultivar of *Eryngium planum* named Blue Ribbon, as illustrated and described.

* * * * *

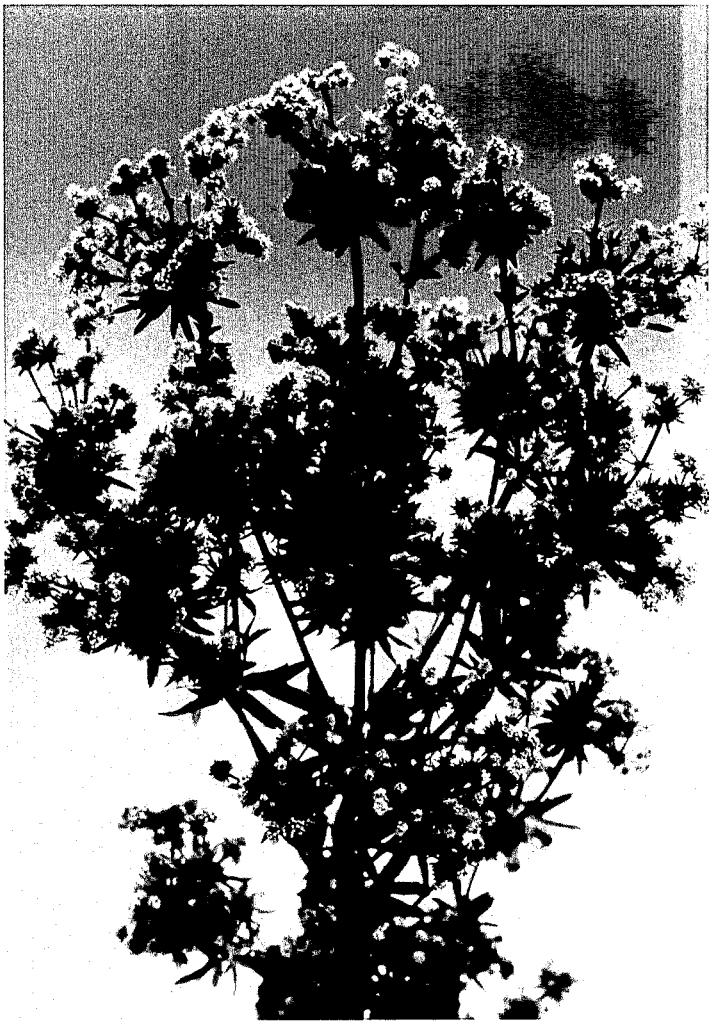

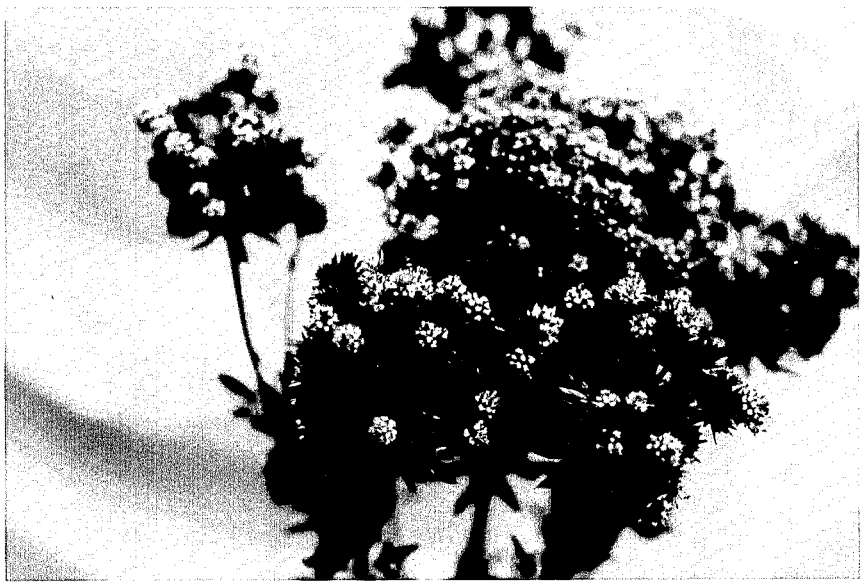

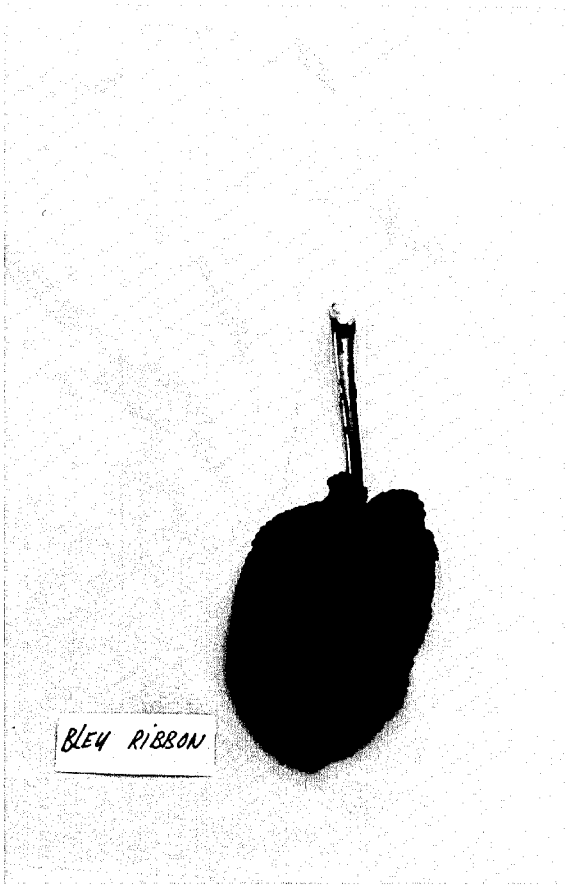
BLEU RIBBON